US009068935B2

(12) United States Patent
Dorman et al.

(10) Patent No.: US 9,068,935 B2
(45) Date of Patent: Jun. 30, 2015

(54) DUAL FET SENSOR FOR SENSING BIOMOLECULES AND CHARGED IONS IN AN ELECTROLYTE

(75) Inventors: Donald Dorman, Carmel, NY (US); Tak Ning, Yorktown Heights, NY (US); Sufi Zafar, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 472 days.

(21) Appl. No.: 12/756,628

(22) Filed: Apr. 8, 2010

(65) Prior Publication Data

US 2011/0247946 A1  Oct. 13, 2011

(51) Int. Cl.
| G01N 27/26 | (2006.01) |
| G01N 33/487 | (2006.01) |
| G01N 27/414 | (2006.01) |
| G01N 27/333 | (2006.01) |
| G01N 27/327 | (2006.01) |

(52) U.S. Cl.
CPC ........ *G01N 27/4145* (2013.01); *G01N 27/3335* (2013.01); *G01N 27/3271* (2013.01); *G01N 27/414* (2013.01)

(58) Field of Classification Search
CPC ............. G01B 27/4145; G01B 27/414; G01B 27/3335; G01B 27/3271
USPC .............. 257/253; 205/789, 792; 204/403.01, 204/416
See application file for complete search history.

(56) References Cited

U.S. PATENT DOCUMENTS

| 3,562,553 A | 2/1971 | Roth |
| 3,766,371 A | 10/1973 | Suzuki |
| 4,173,818 A * | 11/1979 | Bassous et al. ............... 438/286 |
| 4,238,757 A | 12/1980 | Schenck |
| 4,657,658 A | 4/1987 | Sibald |
| 4,984,045 A | 1/1991 | Matsunaga |
| 5,160,597 A | 11/1992 | Colapicchioni et al. |
| 5,309,085 A | 5/1994 | Sohn |
| 6,258,606 B1 | 7/2001 | Kovacs |
| 6,525,354 B2 | 2/2003 | Masleid |

(Continued)

FOREIGN PATENT DOCUMENTS

| DE | 10254158 A1 | 6/2004 |
| JP | 2007533987 | 11/2007 |
| WO | 2008068719 A1 | 6/2008 |

OTHER PUBLICATIONS

"Introductory Electronics for Scientists and Engineers" Second Edition, Robert E. Simpson Ed. 1987 Allyn and Bacon, Chapter 6 pp. 258-284.*

(Continued)

*Primary Examiner* — Luan Van
*Assistant Examiner* — Steven Rosenwald
(74) *Attorney, Agent, or Firm* — Cantor Colburn LLP; Vazken Alexanian

(57) ABSTRACT

A sensor for biomolecules or charged ions includes a substrate; a first node, a second node, and a third node located in the substrate; a gate dielectric located over the substrate, the first node, the second node, and the third node; a first field effect transistor (FET), the first FET comprising a control gate located on the gate dielectric, and the first node and the second node; and a second FET, the second FET comprising a sensing surface located on the gate dielectric, and the second node and the third node, wherein the sensing surface is configured to specifically bind the biomolecules or charged ions that are to be detected.

11 Claims, 4 Drawing Sheets

(56) References Cited

U.S. PATENT DOCUMENTS

| | | | |
|---|---|---|---|
| 6,682,936 | B2 | 1/2004 | Kovacs |
| 6,911,383 | B2 | 6/2005 | Doris et al. |
| 6,956,258 | B2 * | 10/2005 | Peng .............................. 257/298 |
| 7,019,305 | B2 | 3/2006 | Eversmann et al. |
| 7,116,113 | B1 | 10/2006 | Thompsen et al. |
| 7,150,997 | B2 | 12/2006 | Kovacs |
| 7,151,301 | B2 | 12/2006 | Yoo et al. |
| 7,291,496 | B2 | 11/2007 | Holm-Kennedy |
| 7,317,216 | B2 | 1/2008 | Holm-Kennedy |
| 7,357,018 | B2 | 4/2008 | Curry et al. |
| 7,394,263 | B2 | 7/2008 | Pechstein et al. |
| 7,507,675 | B2 | 3/2009 | Zuilhof et al. |
| 2004/0109075 | A1 | 6/2004 | Tsunai |
| 2004/0256655 | A1 | 12/2004 | Kan et al. |
| 2005/0040483 | A1 | 2/2005 | Offenhauser et al. |
| 2005/0053524 | A1 | 3/2005 | Keersmaecker et al. |
| 2005/0068015 | A1 | 3/2005 | Hazucha et al. |
| 2005/0230271 | A1 * | 10/2005 | Levon et al. .................. 205/789 |
| 2006/0145194 | A1 | 7/2006 | Barron et al. |
| 2006/0181925 | A1 | 8/2006 | Specht et al. |
| 2006/0246443 | A1 * | 11/2006 | Bockelmann et al. ............ 435/6 |
| 2006/0272942 | A1 | 12/2006 | Sirringhaus |
| 2007/0080440 | A1 | 4/2007 | Cheng et al. |
| 2007/0159216 | A1 | 7/2007 | Lee et al. |
| 2007/0252176 | A1 | 11/2007 | Shim et al. |
| 2008/0035494 | A1 | 2/2008 | Gomez et al. |
| 2008/0151088 | A1 | 6/2008 | Frey et al. |
| 2008/0303095 | A1 | 12/2008 | Xiong et al. |
| 2008/0315861 | A1 | 12/2008 | Chung et al. |
| 2009/0072313 | A1 * | 3/2009 | Cai et al. ....................... 257/351 |
| 2009/0127589 | A1 | 5/2009 | Rothberg et al. |
| 2010/0164102 | A1 | 7/2010 | Rachmady et al. |
| 2010/0248284 | A1 | 9/2010 | Chen et al. |
| 2011/0033952 | A1 | 2/2011 | Khater et al. |

OTHER PUBLICATIONS

Leobandung et al. J. Vac. Sci. Technol. B (15)6, Nov./Dec. 1997, pp. 2791-2794.*

International Search Report and Written Opinion ; International Application No. PCT/EP2011/052981; International Filing Date: Mar. 1, 2011; Date of Mailing: Jun. 30, 2011; 10 pages.

Khater, et al., U.S. Appl. No. 12/537,063, filed Aug. 6, 2009.

Nakazato et al., CMOS Cascade Source Drain Follower for Monolithically Integrated Biosensor Array, IEICE Trans. Electron, Sep. 2008, pp. 1505-1515, vol. E91-C, No. 9, IEICE.

Stern, et al. Label-free immunodetection with CMOS-compatible semiconducting nanowires, Nature, Feb. 2007, pp. 519-522, vol. 445, NaturePublishingGroup.

Wu et al., Single-crystal metallic nanowires and metal/semiconductor nanowire heterostructures, Letters to Nature, Jul. 2004, pp. 61-65, vol. 430, Nature Publishing Group.

Han, Label-free detection of biomlecules by a field-effect transistor microarray biosensor with bio-functionalized gate surfaces, Dec. 2006 [retrieved on Mar. 17, 2011]. Retrieved from the internet:,URL: http://juwel.fz-juelich.de:8080/dspace/bitstream/2128/2597/1/Juel_4227_Han.pdf; pp. 1-120.

Notification of Transmittal of the International Search Report and the Written Opinion of the International Searching Authority, or the Declaration; PCT/US11/20007;Apr. 6, 20110; pp. 1-13.

YOR920090348US1, U.S. Appl. No. 12/651,504. Non Final Office Action Mailed Mar. 4, 2011; pp. 1-14.

Lee, et al., Ion-Sensitive Field-Effect Transistor for Biological Sensing, Sensors 2003, 9, 7111-7131; doi:10.3390/s90907111 [online], Sep. 7, 2009 [retrieved on Mar. 17, 2011]. Retrieved from the Internet:,URL:http://www.mdpi.com/1424-8220/9/7111/pdf; pp. 7111-7131.

Maher, Electrical Engineering 234 Electrical Engineering Circuit Laboratory, Manual [online], Jun. 1992 [retrieved on Mar. 17, 2011]. Retrieved from the Internet:,URL:http://www.coe.montana.edu/ee/rmaher/teaching/EEngr_234_Labs_maher.pdf>p. 8-1 to 8-20.

Examination Report dated Dec. 23, 2013 for Application No. GB1207849.9; 7 pages.

F. Patolsky et al., Electrical detection of single viruses, PNAS, Sep. 28, 2004, pp. 14017-14022, vol. 101, No. 39, PNAS.

H. Im et al., A dielectric-modulated field-effect transistor for biosensing, Nature Nanotechnology, Jul. 2007, pp. 430-434, vol. 2, Nature Publishing Group.

Hinkle, C.L., et al.; "Enhanced Tunneling in Stacked Gate Dielectrics with Ultra-Thin HfO2 (ZrO2) Layers Sandwiched Between Thicker SiO2 Layers"; Surface Science 566-268; p. 1185-1189; 2004.

Huang, et al. "Development of Active Matrix Biosensor Array for Cell Screening". Proc. of IEEE Sensors 2004.

International Search Report and Written Opinion dated Jun. 30, 2011 for PCT Application No. PCT/EP2011/052981.

K. Nakazato, et al. "CMOS Cascode Source-Drain Follower for Monolithically Integrated Biosensor Array". IEICE Trans. Electron., vol. E91-C, No. 9 Sep. 2008. pp. 1505-1515.

Papadopoulos, S., et al.; "Protein Diffusion in Living Skeletal Muscle Fibers: Dependence on Protein Size, Fiber Type, and Contraction"; Biophysical Journal; vol. 79; p. 2084-2094; Oct. 2000.

* cited by examiner

400

FUNCTIONALIZE SENSING SURFACE
401

PLACE ELECTROLYTE ON SENSING SURFACE
402

MAKE ELECTRICAL CONNECTIONS TO CONTROL GATE, SENSOR NODE, AND CONTROL NODE
403

BIOMOLECULES IN ELECTROLYTE BIND TO SENSING SURFACE
404

DETERMINE CHANGE IN DRAIN CURRENT BETWEEN SENSOR NODE AND CONTROL NODE
405

DETERMINE AMOUNT OF BIOMOLECULES PRESENT IN ELECTROLYTE BASED ON DETERMINED CHANGE IN DRAIN CURRENT
406

FIG. 4

DUAL FET SENSOR FOR SENSING BIOMOLECULES AND CHARGED IONS IN AN ELECTROLYTE

FIELD OF INVENTION

This disclosure relates generally to the field of sensing of biomolecules and charged ions in an electrolyte solution.

DESCRIPTION OF RELATED ART

A field effect transistor (FET), comprising a source, a drain, and a gate, may be used as a sensor for various types of biomolecules, including but not limited to charged ions, such as H+ or Ca++, proteins, glucose, or viruses, by using an electrolyte containing the biomolecules as the FET gate (see P. Bergveld, Sensors and Actuators B 88 (2003) 1-20, for further information). In operation, a voltage may be applied to the FET gate electrolyte by immersing an electrode into the electrolyte, and connecting the electrode to a voltage source. The presence of the electrode may cause the sensor to have a relatively cumbersome setup, and may limit miniaturization and automation of the sensor. The electrode, which may comprise a silver wire coated with a silver chloride layer, may also cause reliability issues in the sensor over time, due to chemical changes in the electrode material that may occur with prolonged use.

A FET based-sensor that does not require an electrode immersed in the electrolyte may comprise a back-gated silicon nanowire FET structure (See E. Stern et al, Nature, Vol. 445, page 519 (2007) for further information). A back gated FET uses a layer of buried oxide as the gate dielectric. The buried oxide may be relatively thick, resulting in a relatively large sub-threshold slope (greater than 300 mV/decade) and high threshold voltages, and as result, the sensitivity of the sensor may be degraded and the sensing voltage is high. In order to improve sensitivity, the silicon nanowire diameters may be made increasingly thin; however, a relatively thin silicon nanowire may lead to yield issues in sensor fabrication. In order to lower the sensing voltage, the thickness of the buried oxide may be made thinner and the fixed charge density in the buried oxide layer may be reduced. The fabrication processes for thin silicon nanowires and thin buried oxide layer with reduced fixed charge density may be relatively complex and costly compared to fabrication process for regular FETs.

SUMMARY

In one aspect, a sensor for biomolecules or charged ions includes a substrate; a first node, a second node, and a third node located in the substrate; a gate dielectric located over the substrate, the first node, the second node, and the third node; a first field effect transistor (FET), the first FET comprising a control gate located on the gate dielectric, and the first node and the second node; and a second FET, the second FET comprising a sensing surface located on the gate dielectric, and the second node and the third node, wherein the sensing surface is configured to specifically bind the biomolecules or charged ions that are to be detected.

In one aspect, a method for operating a sensor for biomolecules or charged ions, the sensor comprising a first field effect transistor (FET) and a second FET, wherein the first FET and the second FET comprise a shared node includes placing an electrolyte containing the biomolecules or charged ions on a sensing surface of the sensor, the electrolyte comprising a gate of the second FET; applying an inversion voltage to a gate of the first FET; making a first electrical connection to an unshared node of the first FET; making a second electrical connection to unshared node of the second FET; determining a change in a drain current flowing between the unshared node of the first FET and the unshared node of the second FET; and determining an amount of biomolecules or charged ions contained in the electrolyte based on the determined change in the drain current.

Additional features are realized through the techniques of the present exemplary embodiment. Other embodiments are described in detail herein and are considered a part of what is claimed. For a better understanding of the features of the exemplary embodiment, refer to the description and to the drawings.

BRIEF DESCRIPTION OF THE SEVERAL VIEWS OF THE DRAWINGS

Referring now to the drawings wherein like elements are numbered alike in the several FIGURES:

FIG. 4 illustrates an embodiment of a method of operating a dual FET sensor.

DETAILED DESCRIPTION

Embodiments of systems and methods for a dual FET sensor for biomolecules and charged ions are provided, with exemplary embodiments being discussed below in detail. A FET-based sensor structure may comprise two serially connected n-type or p-type metal oxide field effect transistors (MOSFETs, or FETs), where the first FET is a control FET and the second FET is a sense FET having an electrolyte as the gate. The control FET and the sense FET may share a node. The gate dielectric surface of the sense FET may be functionalized such that the surface of the gate dielectric specifically binds the type of biomolecules that the dual FET sensor is used to detect. The biomolecules in the electrolyte bind to the functionalized gate dielectric surface of the sense FET, causing a change in a drain current of the sensor. An amount of biomolecules that are present in the electrolyte may be determined based on the change in the drain current. Use of a dual FET sensor eliminates the need to immerse an electrode in the electrolyte.

Figure 1:
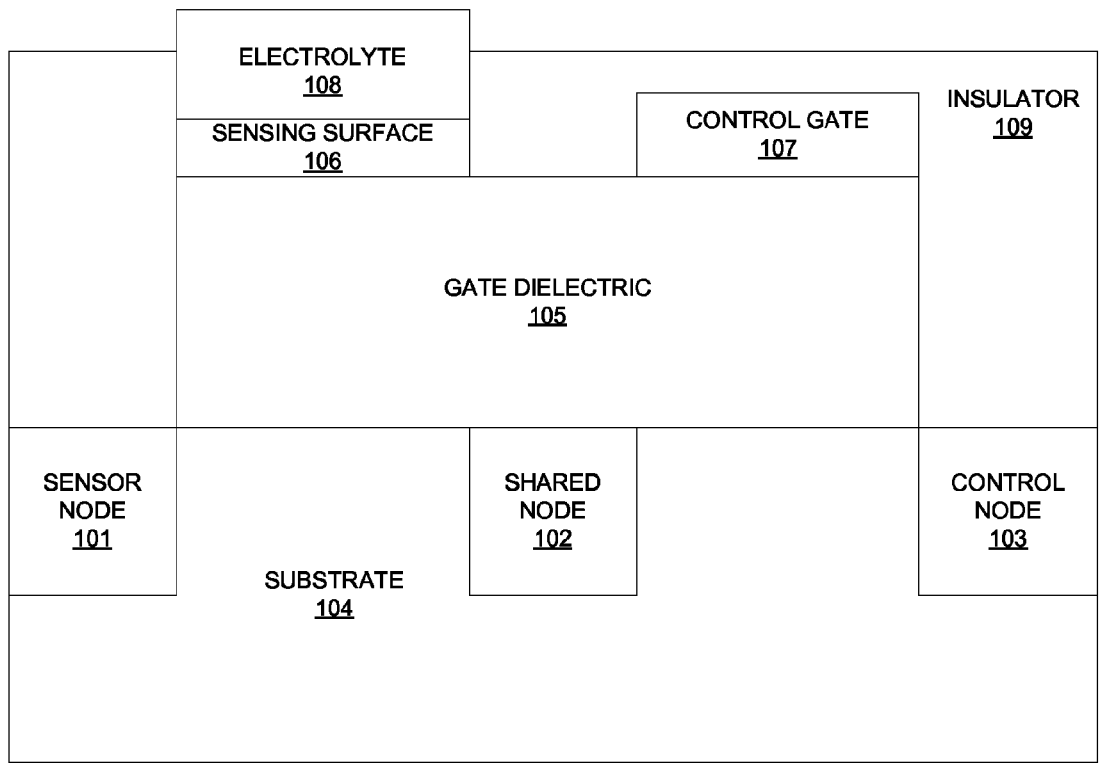
FIG. 1 illustrates an embodiment of a dual FET sensor.

FIG. 1 illustrates an embodiment of a dual FET sensor 100, comprising a control FET and a sense FET. The sense FET comprises shared node 102 and sensor node 101, which act as the sense FET source/drain, and a gate comprising the electrolyte 108. The surface of gate dielectric 105 that is in contact with the electrolyte 108 is functionalized to form sensing surface 106. The control FET comprises shared node 102 and control node 103, which act as the control FET source/drain, and control gate 107. The dual FET sensor 100 is built on a substrate 104; sensor node 101, shared node 102, and control node 103 are formed in substrate 104. An insulating material 109 may be located over the substrate 104. Gate dielectric 105 is located over substrate 104, sensor node 101, shared node 102, and control node 103. In operation, electrical connections are made to sensor node 101, control node 103, and control gate 107, which may comprise metal lines (not shown), and a drain current ($I_d$) flows through dual FET sensor 100 between sensor node 101 and control node 103.

Figure 2:
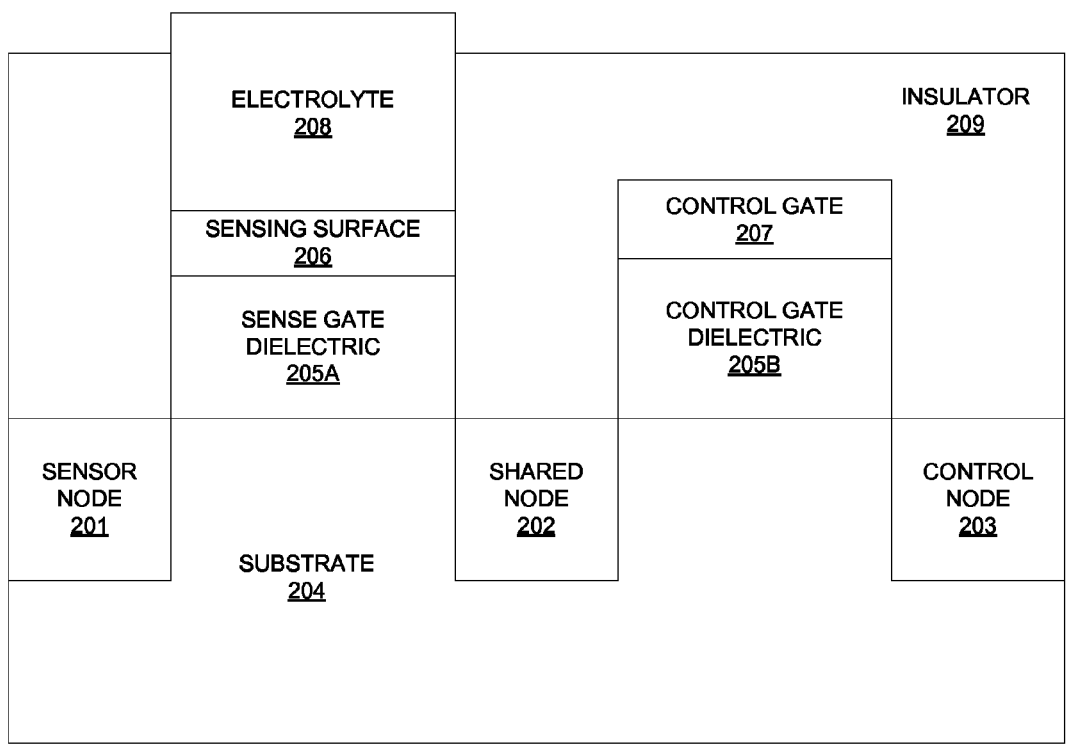
FIG. 2 illustrates an embodiment of a dual FET sensor.

FIG. 2 illustrates an alternate embodiment of a dual FET sensor 200. Dual FET sensor 200 also comprising a control FET and a sense FET. The sense FET comprises shared node 202 and sensor node 201, which act as the sense FET source/drain, and a gate comprising the electrolyte 208 on sense gate dielectric 205A. The surface of gate dielectric 205A that is in contact with the electrolyte 208 is functionalized to form sensing surface 206. The control FET comprises shared node 202 and control node 203, which act as the control FET source/drain, and control gate 207 on control gate dielectric 205B. The dual FET sensor 200 is built on a substrate 104; sensor node 201, shared node 202, and control node 203 are formed in substrate 204. An insulating material 209 may be located over the substrate 204. In operation, electrical connections, which may comprise metal lines (not shown), are made to sensor node 201, control node 203, and control gate 207, and a drain current ($I_d$) flows through dual FET sensor 200 between sensor node 201 and control node 203.

Figure 3:
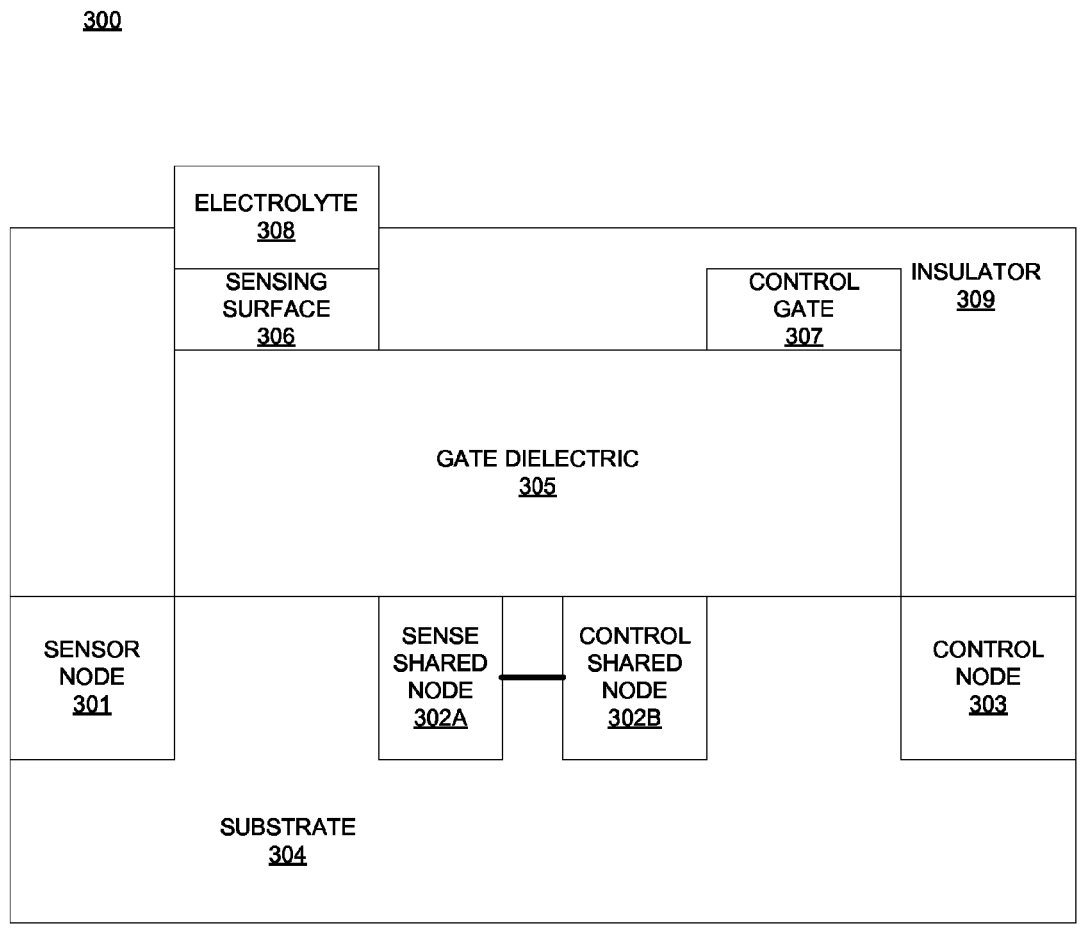
FIG. 3 illustrates an embodiment of a dual FET sensor.

FIG. 3 illustrates an alternate embodiment of a dual FET sensor 200. Dual FET sensor 300 also comprising a control FET and a sense FET. The sense FET comprises sense shared node 302A and sensor node 301, which act as the sense FET source/drain, and a gate comprising the electrolyte 308 on gate dielectric 305. The surface of gate dielectric 305 that is in contact with the electrolyte 308 is functionalized to form sensing surface 306. The control FET comprises control shared node 302B and control node 303, which act as the control FET source/drain, and control gate 307 on gate dielectric 205. Sense shared node 302A is connected to control shared node 302B. The dual FET sensor 300 is built on a substrate 304; sensor node 301, shared nodes 302A-B, and control node 303 are formed in substrate 304. An insulating material 309 may be located over the substrate 304. In operation, electrical connections, which may comprise metal lines (not shown), are made to sensor node 301, control node 303, and control gate 307, and a drain current ($I_d$) flows through dual FET sensor 300 between sensor node 301 and control node 303.

The control gate (107, 207, and 307) may comprise polysilicon or a metal in some embodiments. The sensor node (101, 201, 301), shared node (102, 202, 302A-B), and control node (103, 203, 303), each have the same doping type (n+-type or p+-type) in some embodiments. Substrate 104, 204, and 304 may comprise bulk silicon or silicon-on-insulator, and may have a doping type (n-type or p-type) that is opposite the doping type of the nodes (101-103, 201-203, 301-303) in some embodiments. The gate dielectric (105, 205A-B, 305) may comprise $SiO_2$, SiON, a high-k material, or a bilayer of SiO2 and high k with an equivalent oxide thickness (EOT) greater than 20 angstroms (A) in some embodiments.

FIG. 4 illustrates an embodiment of a method of operating a dual FET sensor 100. FIG. 4 is discussed with respect to FIG. 1; method 400 may also be used in conjunction with the dual sensor FETs 200 and 300 shown in FIGS. 2 and 3. In block 401, gate dielectric surface of the sense FET is functionalized to form the sensing surface 106. Functionalizing of the surface of gate dielectric 105 to form the sensing surface 106 may comprise coating the gate dielectric surface of the sense FET with antibodies or an appropriate chemical that may specifically bind to the particular biomolecules that the sensor is being used to detect in some embodiments. In block 402, electrolyte 108 is placed on sensing surface 106. In block 403, electrical connections are made to control gate 107, sensor node 101, and control node 103. The electrical connections may be made via metal lines connected to each of control gate 107, sensor node 101, and control node 103. A gate voltage is applied to control gate 107 that is sufficient to turn on the control FET. The gate voltage may comprise a constant inversion voltage, and may be between about |1.0| volts (V) and |1.5| V in some embodiments. The control node 103 may be held at a constant voltage $V_d$, which may be about 0.1 V in some embodiments. The sensor node 101 may be held at about 0 V in some embodiments. The shared node 102 and the sense FET gate comprising electrolyte 108 are left floating. In block 404, biomolecules in electrolyte 108 bind to the sensing surface 106. The biomolecules bound to sensing surface 106 causes a change in the workfunction at the interface between the sensing surface 106 and the electrolyte 108, which in turn causes a change in the $I_d$ that flows between the sensor node 101 and the control node 103. In block 405, the change $I_d$ is determined. The change in $I_d$ is determined with respect to a drain current that flows through the sensor 100 in the absence of biomolecules. In block 406, an amount of biomolecules present in electrolyte 108 is determined from the change in $I_d$.

The control FET has a channel length, which is the distance between the control node 103 and the shared node 102. The sense FET also has a channel length, which is the distance between the sensor node 101 and the shared node 102. In some embodiments of dual FET sensor 100, a channel length of the control FET may be shorter than a channel length of the sense FET. Further, the control FET has a channel width, which is the width of the conduction channel of the control FET measured alongside control node 103 in a direction perpendicular to the direction of the drain current flow. The sense FET also has a channel width, which is the width of the conduction channel of the sense FET measured alongside sense node 101 in a direction perpendicular to the direction of the drain current flow. In some embodiments of dual FET sensor 100, a channel width of the control FET may be shorter than a channel width of the sense FET.

The technical effects and benefits of exemplary embodiments include detection of biomolecules or ions in an electrolyte without the need to immerse an electrode in the electrolyte.

The terminology used herein is for the purpose of describing particular embodiments only and is not intended to be limiting of the invention. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A sensor for biomolecules or charged ions, comprising:
a substrate;
a sensor node, a single shared node, and a control node located in the substrate;

a gate dielectric located over the substrate, the sensor node, the shared node, and the control node, and comprising SiON;

a control field effect transistor (FET), the control FET comprising a control gate located on the gate dielectric, a control drain disposed in the control node and a control source disposed in the shared node, the control FET having a channel length that is equal to a distance between the control node and the shared node;

an insulating material located directly over the gate dielectric and the control gate; and a sense FET, the sense FET comprising a sensing surface located directly on the SiON of the gate dielectric and configured to act as a gate of the sense FET, a sense drain disposed in the shared node and a sense source disposed in the sensor node, the sense FET having a channel length that is equal to a distance between the sensor node and the shared node, wherein the sensing surface is configured to specifically bind the biomolecules or charged ions that are to be detected;

wherein a number of the biomolecules or charged ions that are to be detected that are binded to the sensing surface is related to a current between the sense source of the sensor node and control drain of the control node, wherein the channel length of the control FET is shorter than the channel length of the sense FET.

2. The sensor for biomolecules or charged ions of claim 1, further comprising an electrolyte comprising biomolecules or charged ions located on the sensing surface.

3. The sensor for biomolecules or charged ions of claim 2, wherein the sensing surface comprises a coating of antibodies or a chemical configured to specifically bind with the biomolecules or charged ions in the electrolyte.

4. The sensor for biomolecules or charged ions of claim 1, wherein the substrate comprises silicon or silicon-on-insulator.

5. The sensor for biomolecules or charged ions of claim 1, wherein the sensor node, shared node, and control node each have the same doping type, and the substrate comprises a doping type that is opposite the doping type of the sensor node, shared node, and control node.

6. The sensor for biomolecules or charged ions of claim 1, wherein the gate dielectric comprises one of $SiO_2$, SiON, a high-k material such as $HfO_2$, and a stack of $SiO_2$/high-k.

7. The sensor for biomolecules or charged ions of claim 1, wherein the gate dielectric has an equivalent oxide thickness (EOT) greater than 20 angstroms (A).

8. The sensor for biomolecules or charged ions of claim 1, wherein the control gate comprises polysilicon or a metal.

9. The sensor for biomolecules or charged ions of claim 1, wherein the control gate is configured to receive a gate voltage, the gate voltage being configured to turn on the control FET.

10. The sensor for biomolecules or charged ions of claim 1, further comprising a first electrical connection to the sensor node, a second electrical connection to the control node; and a third electrical connection to the control gate.

11. The sensor for biomolecules or charged ions of claim 1, wherein a channel width of the control FET is shorter than a channel width of the sense FET.

* * * * *